United States Patent
Bey et al.

(10) Patent No.: US 10,926,373 B2
(45) Date of Patent: Feb. 23, 2021

(54) HONING MACHINE WITH A MACHINE FRAME AND AT LEAST TWO UNITS ARRANGED ON BOTH SIDES OF THE MACHINE FRAME

(71) Applicant: Gehring Technologies GmbH, Ostfildern (DE)

(72) Inventors: Oliver Bey, Esslingen (DE); Rainer Köneke, Nuertingen (DE); Theodor Huettner, Notzingen (DE); Michael Petschi, Hochdorf (DE)

(73) Assignee: GEHRING TECHNOLOGIES GMBH, Ostfildern (DE)

( * ) Notice: Subject to any disclaimer, the term of this patent is extended or adjusted under 35 U.S.C. 154(b) by 290 days.

(21) Appl. No.: 15/147,312

(22) Filed: May 5, 2016

(65) Prior Publication Data

US 2016/0325396 A1    Nov. 10, 2016

(30) Foreign Application Priority Data

May 6, 2015   (DE) ...................... 10 2015 208 330.6

(51) Int. Cl.
  *B24B 41/02*  (2006.01)
  *B24B 41/04*  (2006.01)
  (Continued)

(52) U.S. Cl.
  CPC .......... *B24B 33/02* (2013.01); *B24B 27/0038* (2013.01); *B24B 27/0046* (2013.01);
  (Continued)

(58) Field of Classification Search
  CPC ......... B24B 33/00; B24B 33/02; B24B 33/04;
    B24B 27/0023; B24B 27/0038; B24B
    27/0046; B24B 27/0076; B24B 41/02;
    B24B 41/04; B24B 41/047; B24B
    27/0015; B24B 27/0061
  (Continued)

(56) References Cited

U.S. PATENT DOCUMENTS 1,617,606 A * 2/1927 Pierle ..................... B23Q 37/00
                                                            29/33 P
1,783,019 A * 11/1930 Johnson ................. B24B 33/02
                                                            451/156
(Continued)

FOREIGN PATENT DOCUMENTS

CN    201579467 U    9/2010
CN    202701766 U    1/2013
(Continued)

OTHER PUBLICATIONS

DE202012008938 Machine Generated Translation of Abstract (1page).
(Continued)

*Primary Examiner* — Eileen P Morgan
(74) *Attorney, Agent, or Firm* — Ware, Fressola, Maguire & Barber LLP

(57) ABSTRACT

A honing machine features a stand (1) with at least two feet (3), wherein the stand (1) has an area with two substantially parallel surfaces, and wherein at least one honing spindle (11), another machining spindle (11) or another functional unit is arranged on the two substantially parallel surfaces of the stand (1).

17 Claims, 3 Drawing Sheets

(51) Int. Cl.
*B24B 33/02* (2006.01)
*B24B 27/00* (2006.01)

(52) U.S. Cl.
CPC ...... *B24B 27/0061* (2013.01); *B24B 27/0076* (2013.01); *B24B 41/02* (2013.01); *B24B 41/04* (2013.01)

(58) Field of Classification Search
USPC .......................................... 451/65, 340, 361
See application file for complete search history.

(56) References Cited

U.S. PATENT DOCUMENTS

| | | | | |
|---|---|---|---|---|
| 2,294,184 | A * | 8/1942 | Johnson | B24B 33/02 451/151 |
| 2,356,223 | A * | 8/1944 | Crompton, Jr. | B24B 33/02 451/151 |
| 2,747,336 | A * | 5/1956 | Peden | B24B 33/02 451/150 |
| 2,805,521 | A * | 9/1957 | Hasty | B24B 33/022 451/124 |
| 2,939,251 | A * | 6/1960 | Greening | B24B 1/04 451/124 |
| 3,393,472 | A * | 7/1968 | Sunnen | B24B 33/02 451/155 |
| 3,490,318 | A * | 1/1970 | McKenzie | B23B 29/20 82/173 |
| 3,637,469 | A * | 1/1972 | Ellis | B24B 33/02 205/93 |
| 4,180,945 | A * | 1/1980 | Zimmerman | B23Q 1/48 408/234 |
| 4,423,567 | A * | 1/1984 | Raven, III | B24B 33/02 451/124 |
| 4,557,640 | A * | 12/1985 | Rottler | B23B 41/12 29/26 A |
| 4,607,460 | A * | 8/1986 | Mushardt | B24B 51/00 451/226 |
| 4,907,372 | A * | 3/1990 | Molitor | B24B 33/02 451/130 |
| 5,439,431 | A * | 8/1995 | Hessbruggen | B23Q 1/00 483/14 |
| 5,443,338 | A * | 8/1995 | Huber | B23F 19/007 409/37 |
| 6,302,315 | B1 * | 10/2001 | Thompson | B23K 20/123 228/112.1 |
| 6,357,094 | B1 * | 3/2002 | Sugimoto | B23Q 1/012 29/26 A |
| 6,798,088 | B2 * | 9/2004 | Hsu | B23Q 1/012 310/12.13 |
| 6,920,678 | B2 * | 7/2005 | Ooe | B23Q 7/1426 29/33 P |
| 7,273,335 | B2 * | 9/2007 | Furuhashi | B23Q 1/012 409/191 |
| 7,354,227 | B2 * | 4/2008 | Ramnauth | B23P 23/02 29/33 K |
| 7,371,149 | B2 * | 5/2008 | Cloutier | B23Q 17/2233 451/5 |
| 7,566,193 | B2 * | 7/2009 | Haj-Fraj | B23Q 1/4876 409/216 |
| 8,210,907 | B2 * | 7/2012 | Walter | B24B 27/0023 451/61 |
| 8,662,802 | B2 * | 3/2014 | Mischler | B23Q 1/015 408/185 |
| 9,011,053 | B2 * | 4/2015 | Sugiyama | B23Q 1/012 409/185 |
| 9,168,633 | B2 * | 10/2015 | Peng | B24B 51/00 |
| 2002/0131836 | A1 * | 9/2002 | Ferrari | B23Q 1/012 409/212 |
| 2004/0109734 | A1 * | 6/2004 | Ooe | B23Q 7/1478 408/3 |
| 2004/0151556 | A1 * | 8/2004 | Ferrari | B23Q 17/2233 409/201 |
| 2004/0255736 | A1 * | 12/2004 | Nakamura | B23Q 1/015 82/149 |
| 2006/0089087 | A1 * | 4/2006 | Koch | B23Q 7/1405 451/11 |
| 2006/0291971 | A1 * | 12/2006 | Tanoue | B23Q 1/012 409/202 |
| 2007/0298685 | A1 * | 12/2007 | Cloutier | B23Q 17/2233 451/5 |
| 2009/0121113 | A1 * | 5/2009 | Yasuda | B23B 3/065 248/429 |
| 2010/0210190 | A1 * | 8/2010 | Walter | B24B 27/0023 451/61 |
| 2012/0152069 | A1 * | 6/2012 | Hyatt | B23B 29/03446 82/1.11 |
| 2016/0256980 | A1 * | 9/2016 | Bellanger | B65G 65/00 |

FOREIGN PATENT DOCUMENTS

| | | | |
|---|---|---|---|
| CN | 203156371 U | 8/2013 | |
| CN | 103737417 A | 4/2014 | |
| CN | 204057251 U | 12/2014 | |
| DE | 10041653 A1 | 3/2002 | |
| DE | 602004002992 | 6/2007 | |
| DE | 202010000935 U1 | 3/2010 | |
| DE | 102007045619 | 10/2010 | |
| DE | 202012008938 | 11/2012 | |
| DE | 102012201730 | 8/2013 | |
| EP | 1488887 | 12/2004 | |
| EP | 1488887 A1 * | 12/2004 | ............ B23Q 1/015 |
| JP | S59196115 | 11/1984 | |
| JP | 2005131768 A | 5/2005 | |
| JP | 2010155300 | 7/2010 | |
| KR | 101234640 B1 | 2/2013 | |
| WO | 2013117482 | 8/2013 | |
| WO | WO-2014169994 A1 * | 10/2014 | |

OTHER PUBLICATIONS

English Language Abstract of KR101234640B1.
English Language Abstract of CN202701766U.
English Language Abstract of CN203156371U.
English Language Abstract of CN201579467U.
English Language Abstract of CN204057251U.

* cited by examiner

HONING MACHINE WITH A MACHINE FRAME AND AT LEAST TWO UNITS ARRANGED ON BOTH SIDES OF THE MACHINE FRAME

BACKGROUND OF THE INVENTION

1. Field of Invention

This invention relates to honing machines.

2. Description of Related Art

Honing machines are constructed in very different configurations for a plurality of different tasks. Starting from a honing machine with only a vertically arranged spindle, honing machines have developed to linked systems which also perform machining steps going beyond the honing and which take place before or after the actual honing. A machining step that takes place beforehand is, e.g., the fine boring of a bore which is subsequently honed. A machining step which takes place after the honing is, e.g. the brushing and the laser structuring of a previously honed bore.

Therefore, in the context of the invention at times honing spindles are discussed and at times machining spindles are also discussed. Machining spindles are spindles which perform machining steps which take place before or after the honing. The generic concept "spindle" denotes in the context of the invention honing spindles as well as machining spindles.

Although the honing spindles and the machining spindles have achieved a very high state of development, there is still a potential for improvement in the entire system called "honing machine".

SUMMARY OF THE INVENTION

The present invention therefore needs to solve the basic problem of making a honing machine available in which all spindles and auxiliary units such as rotary tables, tool changers, etc. and the workpieces are readily accessible. At the same time the required footprint should be small. Furthermore, scalability, short idle periods and optimal possibilities for loading and unloading are improved.

This problem is solved in accordance with the invention by a honing machine comprising a stand with at least two feet, wherein the stand has an area with two substantially parallel surfaces and wherein at least one honing spindle, one machining spindle or another functional unit is arranged on the two surfaces of the stand. An example for a functional unit in the sense of the invention is a measuring device that detects one or more dimensions of the workpiece before during or after the machining.

In the machine concept according to the invention the stand has a planar and substantially level base structure, wherein at least one honing spindle or a different machining spindle is arranged on both sides of this level base structure. The two spindles are used fastened as it were "back-to-back" on the stand. Therefore, the stand is located in the middle or in the plane of symmetry of the honing machine so that each spindle can be readily reached. This simplifies the maintenance. The concept "plane of symmetry" is not to be understood in a strictly geometrical sense. It will become clear using the FIGS. 1 and 2 that the honing machine and its stand in accordance with the invention have a substantially symmetrical construction.

Because more than one machining spindle or honing spindle can be arranged on each of the two surfaces, the scalability and the flexibility of the honing machine of the invention are very great. In particular the replacement or remodeling of one or more machining spindles is very simple and can be rapidly carried out with the concept of the invention on account of the good accessibility.

In a first embodiment the honing machine comprises a stand with two feet, wherein the stand and the two feet are arranged in a plane. As a result, a very slim honing machine which requires only a small footprint results. This honing machine can comprise two spindles, e.g., on one surface or side of the stand so that a total of 2×2=4 machining spindles or honing spindles can be fastened on one stand. This takes place with a very small footprint relative to the number of spindles.

Another embodiment of the invention provides that the stand comprises three feet, wherein the stand has a T-shaped structure with three ends in a top view and wherein a foot is provided on each of the three ends. Therefore, the stand of the honing machine of the invention is a tripod with a T-shaped structure. It is also sufficiently stable for very difficult machining tasks. Nevertheless, the footprint is very small relative to the capacity and the loadability of the honing machine.

As a rule, it is advantageous if the transverse beam of the T-shaped structure has a length corresponding to the working range of the honing spindles so that the transverse beam does not project more over the actual stand than two spindles arranged on both surfaces of the stand.

In order to be able to flexibly equip the honing machine of the invention with different machining spindles or honing spindles and to be able to also move the spindles relative to a workpiece, at least one guide or receptacle for one or more spindles is provided on each of the two parallel surfaces of the stand. Alternatively, a stationary spindle position is also possible.

In order to achieve an optimal utilization of space, it is provided that a free space is present underneath the stand and between the feet. Several workpieces can be clamped in the free space and then be simultaneously machined by two machining spindles located on the opposing sides of the stand. It is also possible to deliver a workpiece to one or more machining spindles or honing spindles of the machine through this free space. This further increases the flexibility, even though the machine in accordance with the invention only requires a very little footprint.

In an advantageous embodiment of the invention the honing machine comprises a substructure, wherein the feet of the stand are connected to the substructure. This results in a very stiff and rigid structure. Moreover, the modularity of the honing machine of the invention is further improved.

In a further advantageous embodiment of the invention means for handling and/or clamping workpieces is arranged in the free space underneath the stand. It is also possible that the clamping means can move with one of the spindles. This means that means is provided in or in the immediate vicinity of the machining space in order to transport the workpieces into the machining space and subsequently fix them there. The latter can be clamping tables or also indexings with which the workpiece is precisely fixed in its position and is subsequently machined with one or more of the machining spindles arranged on the honing machine of the invention.

The means for handling and/or clamping workpieces can be a rotary table and/or a transport device, in particular a stepped lifting drive or another means known form the prior art.

In order to achieve an effective production with a high yield, at least one tool magazine and/or a tool changer is arranged in another advantageous embodiment of the invention on the substructure or on the stand. This makes it possible to rapidly and readily replace tools when they become worn or when another machining step is to be carried out with other tools.

All devices and systems known from the prior art can be used as tool magazine and as tool changer. In particular, chain magazines, ring magazines or linear magazines can be used. Even in the case of the tool changers all tool receiving systems present in the market can be used. The honing machine of the invention can therefore also be readily integrated in existing manufacturing devices.

In addition to the honing spindles even spindles for fine boring, brushing, boring, abrading and others can be used by the honing machine of the invention.

Other advantages and advantageous embodiments of the invention can be gathered from the following drawings, their description and the claims. All features disclosed in the drawings, their description and the claims can be significant for the invention individually as well as in any combination with each other.

BRIEF DESCRIPTION OF THE DRAWING

The drawing includes FIGS. 1-3, as follows.

DETAILED DESCRIPTION OF THE BEST MODE OF THE INVENTION

Figure 1:
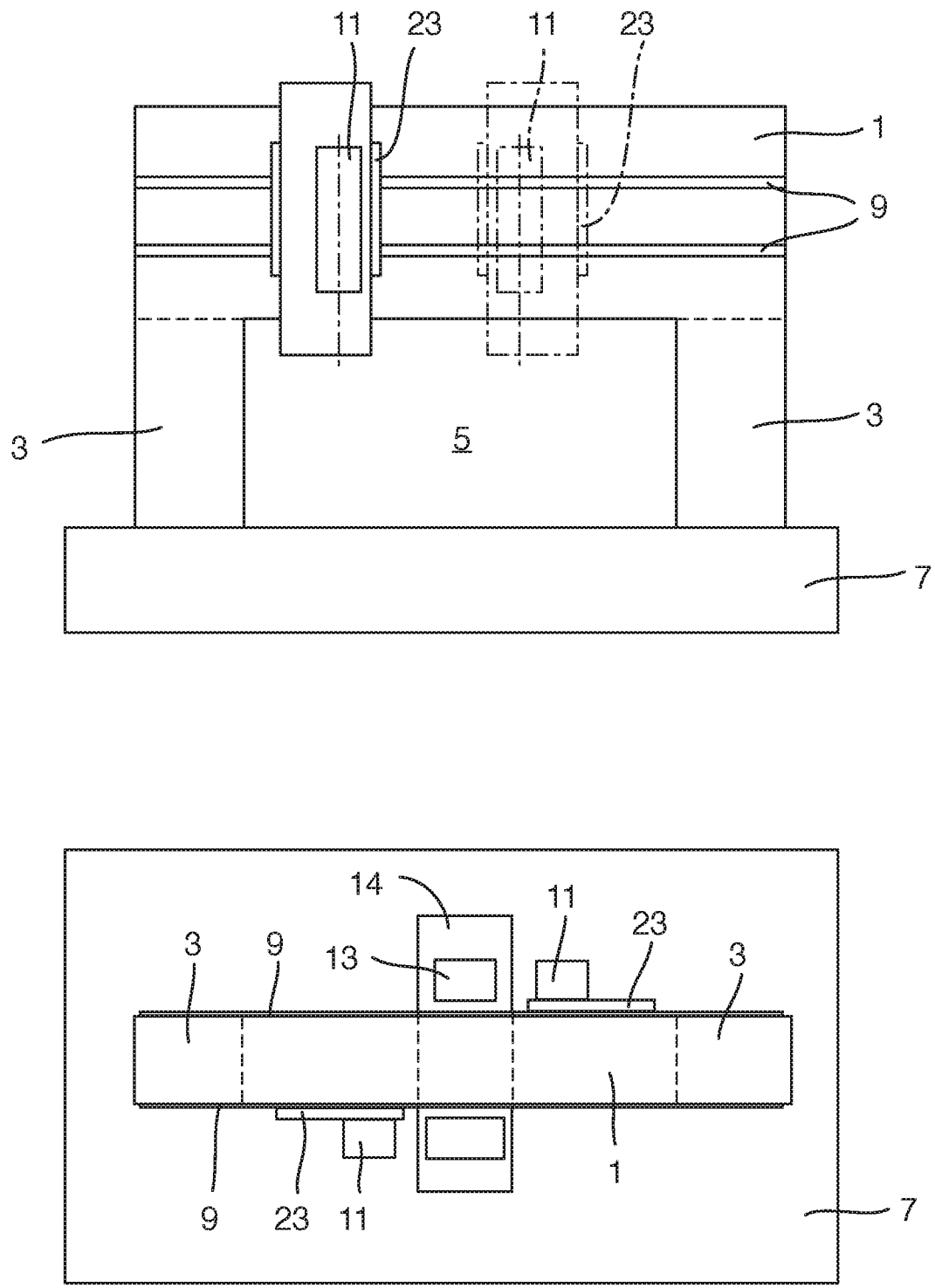
FIG. 1 shows a schematic view of a first exemplary embodiment of a stand of a honing machine according to the invention.

FIG. 1 schematically shows a stand 1 with two feet 3 in a side view and a top view. Stand 1 and feet 3 are constructed as a rule as a one-part welded construction. Depending on the size of the machine, the feet 3 can also be screwed to the stand 1.

The feet 3 of the stand 1 are connected to a substructure 7. Tool changers, transport devices, clamping means and to magazines or other operating means for additional processes (not shown) can be arranged on the substructure 7.

Receptacles 9 are constructed on the stand 1 which serve to receive one or more spindles 11 (honing spindles or other machining spindles). The receptacles 9 can be designed in such a manner that the spindles 11 can be moved between two machining steps along the receptacle, i.e., in a horizontal direction in FIG. 1 until they reach the new site of use. Alternatively, it is also possible to arrange the spindles 11 firmly on the stand 1, e.g., by screws.

A top view of the stand 1 of the invention is shown in the lower part of FIG. 1. It is clear from it that the stand 1 and the feet 3 show a substantially level structure and that receptacles 9 are arranged on both sides of this level structure 1. One or more spindles 11 can be arranged on these receptacles 9 arranged on both sides of the stand 1. The symmetrical structure of the honing machine of the invention becomes very clear from the top view. Because the stand 1 is arranged in the plane of symmetry, the spindles outwardly project in both directions and are therefore readily accessible. Furthermore, only a small footprint is required.

A free space 5 is present between the feet 3 and the receptacle 9 in the side view of FIG. 1 below the stand 1 which free space also limits the machining space of the honing machine at the same time. Workpieces (not shown) can be transported through the free space 5 into the machining space until they reach the site at which they are to be machined. They are then clamped there in a traditional manner, e.g. in a receptacle manufactured for this purpose or in an index clamping device. As soon as the workpiece has been correctly clamped, one or more of the spindles 11 can begin with the machining.

The spindles 11 are designed in such a manner that they operate in a vertical direction, as is the case with many honing spindles.

In the top view a workpiece transport 14 with at least one workpiece 13 extending through under the stand 1 is indicated by a dotted line for purposes of illustration. This creates the possibility with a honing machine in accordance with the invention of machining two workpieces simultaneously or sequentially with the spindles 11 arranged on both sides of the stand 1.

It is also clear that in spite of the very small footprint of the actual honing machine large and long workpieces 13 can be machined although the jutting out of the honing spindles and machining spindles 11 is very slight. This results in a high degree of stiffness of the honing machine which has a positive effect on the quality of the machining and the cycle times.

In the exemplary embodiment shown in FIG. 1 a total of two honing and machining spindles 11 are arranged on the receptacles 9 of the stand 1. Each of the honing and machining spindles 11 can be moved along the receptacles 9, i.e., in a horizontal direction relative to the stand 1. As soon as the spindles 11 have reached the desired position they are stopped and are then ready to be used for a honing machining or another machining step. This transverse movement of the spindles 11 takes place with the aid of a transverse carriage 23. The transverse carriage 23 serves to position the spindles 11 over the machining position and the tool changer 21.

Figure 2:
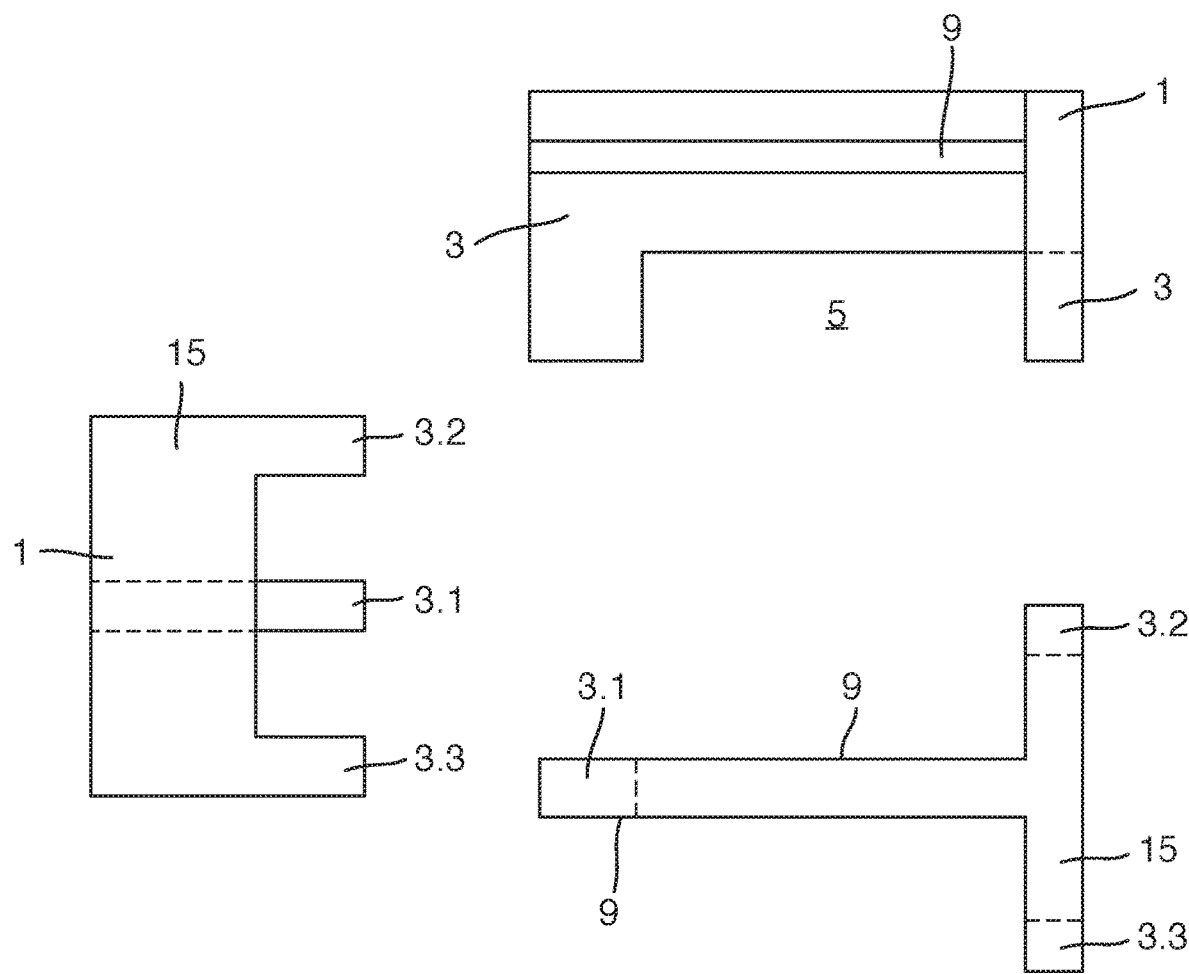
FIG. 2 shows a second exemplary embodiment of the stand of a honing machine according to the invention.

FIG. 2 shows another exemplary embodiment of a honing machine according to the invention. In this exemplary embodiment the stand 1 comprises three feet 3. The stand 1 has a T-shaped structure in a top view. A foot 3.1 to 3.3 is provided on the ends of this T-shaped structure. For reasons of clarity, neither spindles 11 nor a workpiece 13 are shown in the FIG. 2. However, it is clear that even in this very robust structure in the manner of a tripod there is a large free space 5 underneath the stand and between the feet 3.1 to 3.3.

The T-shaped structure of the stand 1 is subdivided for the explanation into the actual stand 1 and a transverse beam 15. The feet 3.2 and 3.3 are arranged underneath the transverse beam 15. The receptacles 9 are present on the actual stand 1. The stand 1 is extremely robust in this T-shaped structure. Nevertheless, the free space 5 is very large and workpieces can be introduced from various directions into the free space 5 and into the machining space. It is possible, among other things, to move a workpiece through between the feet 3.2 and 3.3 into the free space 5. Of course, a workpiece 13 can also be brought into the free space 5 from the sides of the stand 1.

Figure 3:
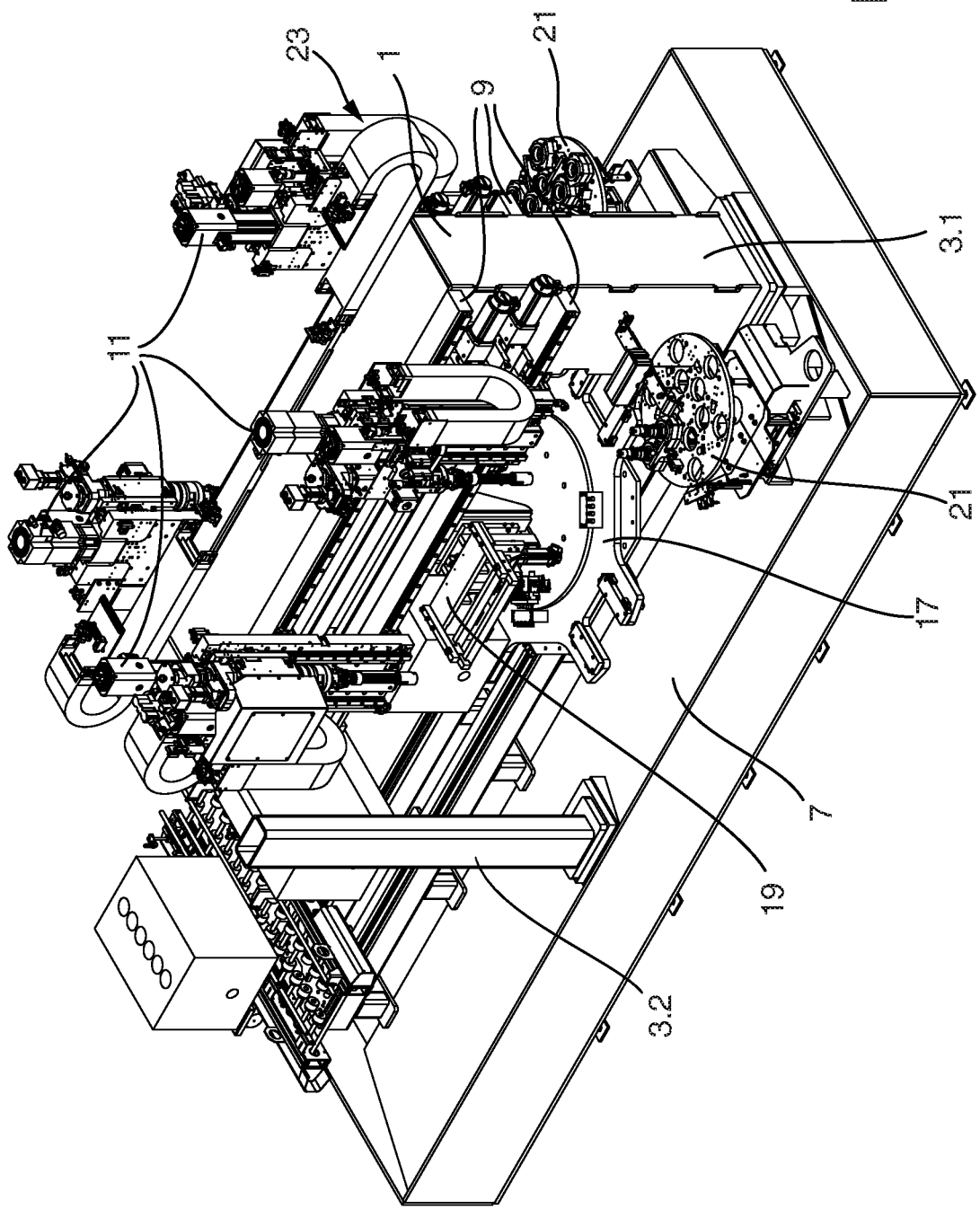
FIG. 3 shows a honing machine according to the invention.

FIG. 3 shows a honing machine with a stand 1 which comprises three feet 3 and therefore corresponds structurally to the exemplary embodiment of FIG. 2.

In the exemplary embodiment shown in FIG. 3 a total of four honing and machining spindles 11 are arranged on the receptacles 9 of the stand 1. Each of the four honing and machining spindles 11 can move along the receptacles 9, i.e., in a horizontal direction, relative to the stand 1. As soon as the spindles 11 have reached the desired position they are stopped and are then ready to be used for a honing machining or another machining step.

A rotary table 17 is present in the free space 5 underneath the stand 1 and between the feet 3. The rotary table 17 is connected to the substructure 7 and serves to rapidly and reliably bring the workpieces into the position provided for the machining. The rotary table 17 can be provided with individual replacement parts adapted to the workpiece 13 to be machined.

Alternatively, the rotary table 17 can also be arranged on the stand 1. The direction of movement, i.e., the axis of rotation of the rotary table 17 can run vertically. Finally, at least one device 19 for clamping or holding down workpieces 13 is present. This device 19 can comprise a zero point clamping system and/or be provided with mechanically, electrically, pneumatically or hydraulically driven devices.

The devices 19 for clamping can be fastened on the rotary table 17, the stand 1 for the spindles 11, the substructure 7 or also on the spindles 11 in such a manner that they move with them.

Furthermore, tool changers 21 are present which can be constructed as a round magazine, linear magazine, surface magazine or chain magazine. The tool changer 21 executes a translatory or rotary relative movement to the spindle axis for changing the tool. FIG. 3 shows a tool changer 21 in the form of a round magazine by way of example.

The tool changer or changers 21 can be fastened on the stand 1, the substructure 7, the foot 3 or the spindles 11.

The transverse movement of the spindles 11 takes place with the aid of a transverse carriage 23 which cannot be well recognized in FIG. 3 because most of it is covered by the spindles 11 and their periphery. The cross carriage 23 serves to position the spindles 11 over the machining position and the tool changer 21.

As already mentioned, it is also possible to connect the spindles 11 rigidly to the stand 1. It is also possible to arrange two or more spindles 11 on a transverse carriage 23 and to move them in common into the machining position. In this case the gauge for bore holes of the spindles 11 connected to each other is manually or automatically adjusted via a separate adjusting unit.

The feed of the workpieces takes place via a feed unit to the rotary table 17. The feed can be designed as a lifting-rotary movement 24. Other loading possibilities of the rotary table 17 are also possible via alternative loading devices such as, e.g., a stepped lifting transport, shuttle, gantry or robot or manually. This emphasizes the flexibility of the concept of the invention.

It is very clear from FIG. 1 in FIG. 3 that all structural components of the honing machine of the invention are very readily accessible because the carrying structure, namely, the stand 1 with the feet 3 is arranged to a certain extent in the middle of the machine and all attached parts project outwardly from this stand 1 arranged in the middle. This makes possible the very good accessibility to all attached parts, whether they are spindles 11, drives, tool changers 21, rotary table 17 and others. At the same time, it is also clear that the space requirement for the machine of the invention is extremely small relative to the size of the workpieces to be machined.

PARTS LIST 1 stand
3 feet
5 free space
7 substructure
9 receptacles
11 spindles (honing spindles or other machining spindles)
14 workpiece transport
15 transverse beam
17 rotary table
19 device for clamping or holding down
21 tool changer
23 transverse carriage
24 feed (with lifting-rotary movement)

THE SCOPE OF THE INVENTION

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

The invention claimed is:

1. A system comprising:
   a T-shaped stand (1) with three feet (3.1, 3.2, 3.3), wherein the T-shaped stand comprises:
      a transverse beam (15) comprising two ends, each of the two ends having one of the three feet extending vertically therefrom; and
      an elongated beam extending horizontally from the transverse beam and comprising an end opposite the transverse beam having one of the three feet extending vertically therefrom; and
   wherein the elongated beam of the stand (1) has two substantially parallel surfaces on opposite sides of the elongated beam, and wherein at least one honing spindle is arranged on at least one of the two substantially parallel surfaces and;
   wherein the system further comprises:
      a substructure (7) to which the three feet (3) of the stand (1) are connected;
      means for clamping workpieces (13), provided on the substructure; and
      an elongated transport device that is on the substructure and arranged in a free space (5) underneath said transverse beam and the elongated beam, and between the three feet (3), and extending in parallel to the elongated beam.

2. The system according to claim 1, characterized in that the system comprises a plurality of spindles including the at least one honing spindle, wherein each of the plurality of spindles is associated with a spindle receptacle (9), and each of the two parallel surfaces comprises at least one of the plurality of spindles and associated spindle receptacle.

3. The system according to claim 1, wherein the means for clamping workpieces (13) is arranged in the free space (5) underneath the transverse beam and the elongated beam, and between the three feet (3).

4. The system according to claim 3, characterized in that a rotary table (17) is secured to the substructure (7).

5. The system according to claim 3, characterized in that a rotary table (17), is arranged in a free space (5) underneath said transverse beam and the elongated beam, and between the three feet (3).

6. The system according to claim 5, characterized in that one or more of a tool magazine or a tool changer (21) is arranged on the substructure (7).

7. The system according to claim 1, characterized in that the system comprises a plurality of spindles including:
the at least one honing spindle (11) and,
one or more of a spindle for fine boring or a spindle for boring.

8. The system according to claim 1, wherein the elongated beam with two substantially parallel surfaces comprises at least one guide or spindle receptacle.

9. The system according to claim 1, wherein the system comprises a plurality of spindles including the at least one honing spindle (11) and a spindle for abrading.

10. The system according to claim 1, wherein the system comprises a plurality of spindles including the at least one honing spindle (11) and a spindle for rolling.

11. The system according to claim 1, wherein the system comprises a plurality of spindles including the at least one honing spindle (11) and a spindle for shape honing.

12. The system according to claim 1, wherein the system comprises a plurality of spindles including the at least one honing spindle (11) and a spindle for roughening among the plurality of spindles.

13. The system according to claim 1, wherein the system comprises a plurality of spindles including the at least one honing spindle (11) and a spindle for chamfering among the plurality of spindles.

14. The system according to claim 1, wherein system comprises a plurality of spindles including the at least one honing spindle (11) and a spindle for measuring.

15. The system according to claim 6, wherein the tool changer (21) is arranged on the substructure (7) and is a chain magazine, a ring magazine or a linear magazine.

16. The system according to claim 1, wherein the at least one of the spindles is firmly attached to a spindle receptacle by screws.

17. The system according to claim 1, wherein two spindle receptacles (9) are provided on each of the two parallel surfaces.

* * * * *